US009101314B2

United States Patent
Shi (10) Patent No.: US 9,101,314 B2
(45) Date of Patent: Aug. 11, 2015

(54) SYSTEM AND METHOD FOR MONITORING BLADDER AND ABDOMINAL PRESSURES, AND BLADDER FUNCTION RECOVERY SYSTEM

(71) Applicant: SUZHOU DAWEI BIOPHARMA, LTD, Suzhou, JiangSu (CN)

(72) Inventor: Yuenian Shi, Roslyn Heights, NY (US)

(73) Assignee: SUZHOU DAWEI BIPHARMA, LTD., Suzhou, Jiangsu (CN)

( * ) Notice: Subject to any disclaimer, the term of this patent is extended or adjusted under 35 U.S.C. 154(b) by 0 days.

(21) Appl. No.: 14/213,415

(22) Filed: Mar. 14, 2014

(65) Prior Publication Data

US 2014/0200482 A1    Jul. 17, 2014

Related U.S. Application Data

(63) Continuation of application No. PCT/CN2013/071568, filed on Feb. 8, 2013.

(30) Foreign Application Priority Data

Mar. 27, 2012 (CN) .......................... 2012 1 0084275
Mar. 27, 2012 (CN) ...................... 2012 2 0120261 U
Jun. 6, 2012 (CN) .......................... 2012 1 0184356

(51) Int. Cl.
*A61B 5/03* (2006.01)
*A61B 5/20* (2006.01)
*A61F 5/451* (2006.01)
*A61F 5/44* (2006.01)

(52) U.S. Cl.
CPC ................. *A61B 5/205* (2013.01); *A61B 5/036* (2013.01); *A61B 5/208* (2013.01); *A61F 5/4405* (2013.01); *A61F 5/451* (2013.01)

(58) Field of Classification Search
CPC .. A61B 5/205; A61B 5/2018; A61B 5/00517; A61M 39/223
USPC .......................... 600/561; 604/313, 540, 544
See application file for complete search history.

(56) References Cited

U.S. PATENT DOCUMENTS 3,570,488 A * 3/1971 Diskin et al. .................... 604/31
4,184,375 A * 1/1980 Gray ............................. 73/706
(Continued)

FOREIGN PATENT DOCUMENTS

CN       1582848 A    2/2005
CN     200948136 Y    9/2007
(Continued)

OTHER PUBLICATIONS

International Search Report for PCT/CN2013/071568.

*Primary Examiner* — Sean Dougherty
(74) *Attorney, Agent, or Firm* — Lihua Zheng; Proskauer Rose LLP (57) ABSTRACT

Here provided are systems and methods for monitoring bladder and/or abdominal pressures, and a bladder function recovery device. In the systems and methods, the bladder pressure can be detected in real time with a bladder pressure detection unit that is communicated with a urinary catheter. In addition, the abdominal pressure can also be obtained in real time according to the corresponding relationship between the bladder pressure and the abdominal pressure. Furthermore, the bladder function recovery device can be used for bladder function recovery for patients in need.

15 Claims, 9 Drawing Sheets

(56) References Cited

U.S. PATENT DOCUMENTS

| | | | |
|---|---|---|---|
| 4,393,878 A * | 7/1983 | Kahn | 600/561 |
| 4,650,462 A * | 3/1987 | DeSatnick et al. | 604/30 |
| 4,886,059 A * | 12/1989 | Weber | 128/207.15 |
| 5,046,497 A * | 9/1991 | Millar | 600/309 |
| 5,427,114 A * | 6/1995 | Colliver et al. | 600/561 |
| 5,433,216 A * | 7/1995 | Sugrue et al. | 600/591 |
| 6,033,366 A * | 3/2000 | Brockway et al. | 600/486 |
| 6,945,965 B2 * | 9/2005 | Whiting | 604/323 |
| 7,644,722 B2 * | 1/2010 | Christensen et al. | 137/107 |
| 7,726,328 B2 * | 6/2010 | Christensen et al. | 137/107 |
| 7,892,181 B2 * | 2/2011 | Christensen et al. | 600/561 |
| 8,052,671 B2 * | 11/2011 | Christensen et al. | 604/540 |
| 2001/0020162 A1 * | 9/2001 | Mosel et al. | 604/544 |
| 2002/0049425 A1 * | 4/2002 | Mosel et al. | 604/544 |
| 2006/0058702 A1 * | 3/2006 | Christensen et al. | 600/561 |
| 2006/0079804 A1 * | 4/2006 | Sugrue et al. | 600/561 |
| 2007/0038143 A1 | 2/2007 | Christensen et al. | |
| 2007/0179436 A1 * | 8/2007 | Braig et al. | 604/66 |
| 2007/0255090 A1 * | 11/2007 | Addington et al. | 600/29 |
| 2007/0255167 A1 * | 11/2007 | Christensen et al. | 600/561 |
| 2008/0000303 A1 * | 1/2008 | Zwiers et al. | 73/751 |
| 2008/0027373 A1 | 1/2008 | Holte | |
| 2008/0039897 A1 * | 2/2008 | Kluge et al. | 607/17 |
| 2008/0114316 A1 * | 5/2008 | Christensen et al. | 604/323 |
| 2009/0314973 A1 * | 12/2009 | Christensen et al. | 251/61.1 |
| 2011/0046514 A1 * | 2/2011 | Greenwald et al. | 600/573 |
| 2011/0160609 A1 * | 6/2011 | Stone | 600/561 |
| 2013/0030262 A1 * | 1/2013 | Burnett et al. | 600/309 |
| 2014/0200482 A1 * | 7/2014 | Shi | 600/561 |

FOREIGN PATENT DOCUMENTS

| | | |
|---|---|---|
| CN | 101254141 A | 9/2008 |
| CN | 101612038 A | 12/2009 |
| CN | 202654118 U | 1/2013 |

* cited by examiner

SYSTEM AND METHOD FOR MONITORING BLADDER AND ABDOMINAL PRESSURES, AND BLADDER FUNCTION RECOVERY SYSTEM

CROSS REFERENCE TO RELATED APPLICATIONS

This application is a U.S. Continuation under 35 U.S.C. 365(c) of International application No. PCT/CN2013/071568, filed Feb. 8, 2013, which claims priority to earlier-filed Chinese Patent Application Nos. 201210084275.9 filed Mar. 27, 2012, 201220120261.3 filed Mar. 27, 2012, and 201210184356.6 filed Jun. 6, 2012, the disclosure of which applications are incorporated herein by reference.

INVENTION FIELD

The present invention relates to the field of medical devices, specifically to systems and methods for monitoring bladder and abdominal pressure, and for recovering bladder function.

BACKGROUND

Under normal conditions, human intra-abdominal pressure is averagely zero or approximate to zero, but many clinical diseases can cause intra-abdominal pressure to increase. The causes include acute and chronic factors. The former includes large dilatation of hollow organs, edema and exudation of abdominal internal organs, intraperitoneal hemorrhage, and the use of intra-abdominal stuffing. The latter includes the growth of tumors. Continuous increase of intra-abdominal pressure may cause intra-abdominal hypertension. The incidence rate of intra-abdominal hypertension in patients with urination disorder, especially in high-risk surgical patients with urination disorder is generally 5%-40%. In severe cases, it may lead to abdominal compartment syndrome.

The abdominal compartment syndrome may cause a change in the hemodynamic force throughout the body; meanwhile, it may cause incompetence of the circulatory system, respiratory system, urinary system, and digestive system due to breathing restriction. In severe cases, it may cause the patients to suffer from oliguria, anuria, dyspnea, even multiple organ failure, resulting in deadly danger.

For postoperative care for some operation patients, measuring and monitoring the change in abdominal pressure is also an important part to prevent postoperative complications and ensure the patient's uneventful recovery.

In the existing technology, there are several methods for monitoring abdominal pressure as follows:

Direct manometric method: a water manometer or pressure sensor, or a laparoscope pneumoperitoneum machine, or an implanted inflation bag can be used to directly measure the abdominal pressure by placing a catheter or a thick needle in the abdominal cavity;

Indirect manometric method: the abdominal pressure is indirectly measured by measuring the pressure of rectum, stomach, postcava and bladder. The indirect manometric method of bladder pressure is simple and practical, which is known as the gold standard among the indirect manometric methods. Specifically, the method includes firstly emptying the bladder, infusing normal saline, connecting with a pressure sensor, then taking the symphysis position as zero point and measuring at the end of expiration. Other methods: in recent years, there are some new pressure measuring methods, for example, the blood pressure measuring function of the electrocardiogram monitoring (ECG) monitor is used for this purpose.

However, the existing monitoring methods for the abdominal pressure have the following defects:

Although the direct manometric method is accurate for the abdominal pressure measurement, it cannot be effectively promoted due to potential traumatic and infectious risks;

For the indirect manometric method, normal saline must be injected into the bladder before each pressure measurement; only interval pressure measurement can be carried out; air intake or air leakage within the bladder occurs easily; meanwhile, repeated operation may bring great pain and infection risk to the patients;

The pressure measurement method with the ECG monitor often uses blood pressure measuring resource during electrocardiogram monitoring, and is inconvenient to spread in clinical practice.

Therefore, in the clinical care and treatment presently, the above means can only be used when the abdominal pressure data is required indeed according to physical conditions of monitored patients. In other words, current clinical methods cannot monitor the abdominal pressure in real time, whereas the abdominal compartment syndrome cannot be accurately judged just according to the clinical manifestation, and it probably leads to delay and miss of good treatment opportunity because no abdominal pressure is obtained.

SUMMARY OF THE INVENTION

The present invention provides a bladder and abdominal pressure monitoring system and monitoring method, and bladder function recovery device, in order to solve the technical problem that the existing technology is unable to timely and safely know the change in the abdominal pressure.

In one embodiment, the present invention provides a bladder and abdominal pressure monitoring method, comprising the steps of: detecting the bladder pressure in real time with a bladder pressure detection unit communicated with a urinary catheter, and displaying the bladder pressure;

obtaining the abdominal pressure according to the detected bladder pressure, and the corresponding relationship between the bladder pressure and the abdominal pressure;

displaying the abdominal pressure in real time.

Another embodiment of the present invention provides a bladder and abdominal pressure monitoring system, comprising:

a bladder pressure detection unit communicated with the urinary catheter and used for detecting the bladder pressure in real time; a central processing unit, connected with the bladder pressure detection unit and used for obtaining the abdominal pressure according to the detected bladder pressure and the corresponding relationship between the bladder pressure and the abdominal pressure;

a display unit, connected with the central processing unit and used for displaying the bladder pressure and the abdominal pressure in real time.

Another embodiment of the present invention provides a bladder function recovery system, comprising:

a bladder pressure detection unit communicated with the urinary catheter and used for detecting the bladder pressure in real time;

a central processing unit, connected with the bladder pressure detection unit and used for obtaining the abdominal pressure according to the detected bladder pressure and the corresponding relationship between the bladder pressure and the abdominal pressure;

a display unit, connected with said central processing unit and used for displaying the bladder pressure and the abdominal pressure in real time;

a urination device, comprising a drainage bag for collecting urine drained from bladder, a drainage tube communicated with the drainage bag, and a first solenoid valve arranged on the drainage tube, wherein the input end of the first solenoid valve is communicated with the urinary catheter, and the output end thereof is communicated with the drainage tube;

an infusion device used to infuse perfusate into the bladder, and comprising an infusion bag filled with perfusate, an infusion tube used to infuse the perfusate into the bladder, and a third control component arranged on the infusion tube;

The central processing unit is further used for comparing the bladder pressure detected by the bladder pressure detection unit with the maximum preset first bladder pressure threshold and second bladder pressure threshold; according to the comparative results, if the bladder pressure is equal to or higher than the first bladder pressure threshold, switch on the first solenoid valve and switch off the third control component; and if the bladder pressure is lower than or equal to the second bladder pressure threshold, switch off the first solenoid valve and switch on the third control component.

The bladder and abdominal pressure monitoring system, monitoring method and bladder function device provided in the present invention can obtain the abdominal pressure by obtaining the bladder pressure in real time and according to the corresponding relationship between the bladder pressure and the abdominal pressure, so as to realize real-time monitoring of the abdominal pressure and the bladder pressure simultaneously. Thus, the technical problem that the existing technology cannot timely and safely know the change in the abdominal pressure is solved. Furthermore, the bladder function recovery device provided in the present invention can be used for bladder function recovery training of ICU patients, simulate human physiological urination process, maintain the bladder function, prevent or delay urinary system repeated infection, bladder spasms and the change in urinary tract structure and function of patients, so as to avoid the disuse of bladder function and threat of the above conditions to the kidney function, and facilitate the improvement of patient's life quality and prolongation of survival time.

BRIEF DESCRIPTION OF THE DRAWINGS

To describe the technical solutions in the embodiments of the present invention or in the prior art more clearly, the following briefly introduces the accompanying drawings required for describing the embodiments or the prior art. Obviously, the accompanying drawings in the following descriptions show merely some embodiments of the present invention, and persons of ordinary skill in the art may still derive other drawings from the accompanying drawings without creative efforts.

DESCRIPTION OF EMBODIMENTS

In order to clarify the purpose, technical solution and advantages of the embodiments in the present invention, the technical solutions of the embodiments in the present invention will be clearly described in combination with the accompanying drawings in the embodiments. Obviously, the described embodiments are merely part rather than all of the embodiments in the present invention. All other embodiments obtained by ordinary technical personnel without creative efforts based on the embodiments in the present invention shall fall within the protection scope of the present invention.

Embodiment One

Figure 1:
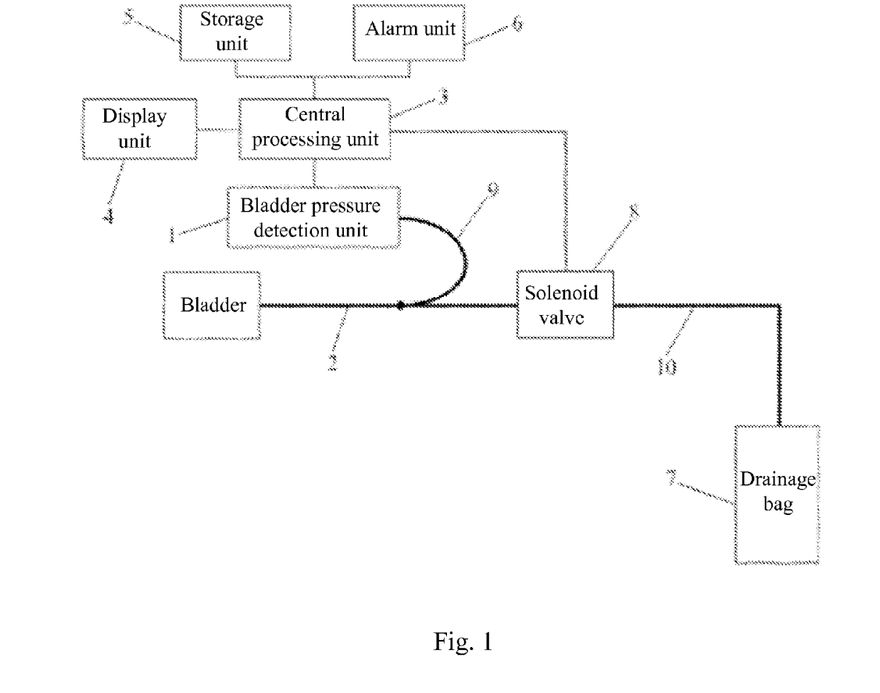
FIG. 1 is a structure diagram of a bladder and abdominal pressure monitoring system in the first embodiment of the present invention.

FIG. 1 is a structure diagram of a bladder and abdominal pressure monitoring system in the first embodiment of the present invention. As shown in FIG. 1, a bladder and abdominal pressure monitoring system provided by the first embodiment of the present invention, comprising:

a bladder pressure detection unit 1, used to communicate with a urinary catheter 2 and collect the bladder pressure in real time, wherein the bladder pressure detecting unit 1 is preferably a low-pressure sensor;

a central processing unit 3, connected with the bladder pressure detection unit 1, and used for obtaining the abdominal pressure according to the detected bladder pressure and the corresponding relationship between the bladder pressure and the abdominal pressure, wherein the central processing unit 3 can be a single-chip microcomputer;

a display unit 4, connected with the central processing unit 3 and used for displaying the bladder pressure and the abdominal pressure in real time, wherein the display unit 4 is preferably an OLED display screen.

The bladder and abdominal pressure monitoring system provided in this embodiment can obtain the abdominal pressure by detecting bladder pressure in real time and according to the corresponding relationship between the bladder pressure and the abdominal pressure, thereby achieving real-time monitoring of the abdominal pressure and the bladder pressure simultaneously. Thus, the technical problem that the existing technology is unable to timely and safely know the change in the abdominal pressure is solved.

Based on the previously mentioned technical solution, the central processing unit 3 in this embodiment is further used to compare the detected pressure with normal pressure of the bladder with pre-stored same urine volume to judge whether the detected bladder pressure is increased or decreased relative to the normal bladder pressure, thus the increase or decrease of the abdominal pressure can be indirectly judged by the increase or decrease of the bladder pressure, so that an alarm unit (refer to the description below) can execute corresponding alarming and prompting operations. For example, the mapping table of the corresponding relationship between the urine volume and normal bladder pressure can be pre-stored in the central processing unit 3. The urine volume of the patient's bladder can be collected in real time by a measuring device frequently used in this field. For example, a portable ultrasonic bladder volume measuring device may be used to detect the current urine volume of the patient's bladder and send the detected current urine volume to the central processing unit 3 through the Bluetooth or WIFI. The central processing unit 3 then finds the normal bladder pressure corresponding to the current urine volume in the mapping table of corresponding relationship between the urine volume and the normal bladder pressure, and takes the corresponding normal bladder pressure as a reference for comparing with the current bladder pressured. The normal bladder pressure is the pressure in a bladder under normal condition before the operation of patients.

As shown in FIG. 1, based on the previously mentioned technical solution, the bladder and abdominal pressure monitoring system in this embodiment further comprises:

a storage unit 5, connected with the central processing unit 3 and used for pre-storing normal pressure of the bladder with the same urine volume;

an alarm unit 6, connected with the central processing unit 3 and used for alarming when the central processing unit 3 has determined that the detected bladder pressure is increased or decreased, wherein the alarm unit 6 may comprise a buzzer and/or a warning light, and is capable of sending out different buzz and/or warning when the bladder pressure is increased or decreased to prompt the patient or the medical worker.

Based on the previously mentioned technical solution, the central processing unit 3 in this embodiment is further used to continue to determine whether the bladder pressure is equal to or higher than the preset pressure when having determined that the bladder pressure is increased. If the bladder pressure is equal to or higher than the preset pressure, the validity of the bladder pressure will be further determined. The preset pressure may be preferably 20 centimeter water column (cmH$_2$O), which is the relatively safe pressure of the bladder. Determination of whether the bladder pressure is valid refers to determination of whether the duration of the bladder pressure is equal to or higher than the preset time. If the pressure duration is equal to or higher than the preset time, the pressure is valid; otherwise, it is invalid. This is because that the bladder pressure sometimes equal to or higher than the preset pressure is caused by the instantaneous external factors or the change of the patient's body position, which does not represent the real pressure within the bladder. Therefore, the duration of the preset pressure should be preset. For example, the preset duration may be set as 10 seconds. Only when the duration of the bladder pressure is equal to or higher than a preset value, the bladder pressure can be proved valid. The addition of validity determination step helps enhance the accuracy and reliability of the bladder pressure detection.

Based on the previously mentioned technical solution, the central processing unit 3 in this embodiment is further used to set a time interval for detecting the bladder pressure by the bladder pressure detection unit 1 in order to determine whether the bladder pressure is equal to or higher than the preset pressure. For example:

When the bladder pressure is less than 30% of the preset pressure, the time interval can be set as 3 minutes;

When the bladder pressure is 30%-60% of the preset pressure, the time interval can be set as 1 minute;

When the bladder pressure is 60%-80% of the preset pressure, the time interval can be set as 30 seconds;

When the bladder pressure is 80%-90% of the preset pressure, the time interval can be set as 15 seconds;

When the bladder pressure is more than 90% of the preset pressure, the time interval can be set as 7.5 seconds.

As shown in FIG. 1, based on the previously mentioned technical solution, the bladder pressure and abdominal pressure monitoring system of the embodiment further comprises a urination device connected with the central processing unit 3. The urination device may comprise:

a drainage bag 7 used to collect urine drained from the bladder, and comprising a drainage tube 10;

a first solenoid valve 8, comprising an input end communicated with the urinary catheter 2 and an output end communicated with the drainage tube 10, and switched on under the control of the central processing unit 3 when the central processing unit 3 has determined that the bladder pressure is valid.

Based on the previously mentioned technical solution, the central processing unit 3 in this embodiment is further used to determine whether the detected bladder pressure reaches the preset minimum threshold during urination. If the bladder pressure reaches the minimum threshold, the central processing unit 3 may switch-off the first solenoid valve 8 to stop urination. The preset minimum threshold is preferably minimum pressure threshold of the monitored abdominal pressure, which cannot only guarantee that the bladder internal pressure always falls within the relatively safe bladder pressure, and is not less than the minimum pressure threshold of the monitored abdominal pressure, so as to realize highly safe low-pressure urine storage and drainage, and real-time monitoring of abdominal pressure. Based on the previously mentioned technical solution, the storage unit 5 in this embodiment is further used to pre-store the above preset pressure, preset time and preset minimum threshold.

Based on the previously mentioned technical solution, the corresponding relationship between the bladder pressure and the abdominal pressure in this embodiment can be represented by a function obtained by the method as follows:

emptying urine in the bladder under normal condition with the urination device in advance, infusing normal saline with total volume not more than 100 ml into the emptied bladder for several times, for example, infusing normal saline with total volume of 100 ml into the emptied bladder for 10 times, 10 ml each time, and after emptying the bladder and infusing normal saline each time, detecting the bladder pressure with the bladder pressure detection unit 1 and the abdominal pressure with an abdominal pressure detection unit (not shown in the drawing) located in the abdominal cavity; taking the bladder pressure collected each time as Y-axis coordinate and the abdominal pressure as X-axis coordinate to draw the relation curve of the bladder pressure and the abdominal pressure, so as to obtain the function of corresponding relationship between the bladder pressure and the abdominal pressure.

In order to guarantee that the above function accurately reflects the linear relation between the bladder pressure and the abdominal pressure, the test is performed on many normal subjects (e.g. 100 subjects) with different ages and sexes, and the precise function of corresponding relationship between the bladder pressure and the abdominal pressure is obtained according to the average values of the collected bladder pressure and abdominal pressure. For example, through detection and calculation, the obtained function of corresponding relationship between the bladder pressure and the abdominal pressure can be the linear function satisfying the following expression:

Y=0.939X+1.482, wherein X represents the abdominal pressure, Y represents the bladder pressure, and 0.939 is correlation coefficient (i.e. slope) and the pressure unit is millimeter of mercury (mmHg).

Thus, as long as the bladder pressure Y detected by the bladder pressure detection unit 1 is substituted into the above expression, the value of the abdominal pressure X can be obtained accordingly.

It should be also noted that, as the bladder volume in a certain range (the filling volume is less than 100 ml) is thought to be only as a passive storage tank with high compliance, like a passive diaphragm, it can transfer the intra-abdominal pressure other than addition of any pressure of its own detrusor muscle. Meanwhile, the studies on correlation between the abdominal pressure and the bladder pressure have been found in some literatures, but so far it is only limited to linear relation thereof in a single fixed volume and has narrow application scope. However, the linear function obtained in the present invention can monitor the abdominal pressure by virtue of the change in bladder pressure within a certain volume range in a dynamic and real-time manner.

Based on the previously mentioned technical solution, the bladder and abdominal pressure monitoring system in this embodiment may further comprise an input setting unit (not shown in the drawing). The input setting unit is connected with the central processing unit 3 and used for the user to input the above preset parameters and perform fine adjustment of the preset parameters according to the user's demand.

Based on the previously mentioned technical solution, the bladder and abdominal pressure monitoring system in this embodiment further comprises a power management unit (not shown in the drawing), and an AC adapter and a rechargeable battery (not shown in the drawing) connected with the power management unit, respectively. The power management unit is connected with the central processing unit 3 and used for selecting the AC adapter or the rechargeable battery to supply power to the whole system, and charge the rechargeable battery via the AC adapter when the rechargeable battery is short of electric quantity.

Based on the previously mentioned technical solution, the alarm unit 6 in this embodiment is further used to give an alarm when the central processing unit 3 has determined that the detected bladder pressure is equal to or higher than the preset pressure and the pressure is valid, wherein the alarm unit 6 may comprise a buzzer and/or a warming light, and is capable of sending out different buzzes and/or alerts when the bladder pressure is close to or reaches to the preset pressure to prompt the patient or the medical worker. For example, when the alarm unit 6 is a buzzer, it may send out two 1-second buzzes when the bladder pressure is close to the preset pressure for the first time; when the bladder pressure continues to be close to the preset pressure, it may send out a 1-second buzz for 1 second and once again a one-minute buzz at intervals of 3 seconds, and the patient can stop it by pressing the key; when the bladder pressure reaches to the preset pressure, it may send out an 8-second buzz. If the patient thinks it is a false alarm within 8 seconds, it may be stopped by pressing the key. If the alarm is not interrupted, the central processing unit 3 will switch on the first solenoid valve 8 for urination after 8 seconds. In addition, when the electric quantity of the rechargeable battery is depleted, the buzzer may also send out a 3-second buzz for one minute and once again 3 seconds later to prompt the patient or the medical worker to replace the battery or charge the battery.

In the bladder and abdominal pressure monitoring system, the drainage tube 10 is communicated with the bladder pressure detection unit 1 via a capillary tube 9. The capillary tube 9 is U-shaped and has both ends with different thickness, wherein the thicker end thereof is connected to the drainage tube 10 and located between the urinary catheter 2 and the first solenoid valve 8, and the other end thereof is connected with the bladder pressure detection unit 1. Furthermore, the capillary tube 9 is filled with pressure transmission medium so that the bladder pressure detection unit 1 does not directly contact with urine in the urinary catheter, wherein the pressure transmission medium can be air or silicone oil, and make the bladder pressure detection unit 1 not directly contact with urine in the urinary catheter 2 while detecting the bladder pressure. Therefore, for different patients, there is no need to replace the bladder pressure detection unit 1, thereby greatly reducing the cost for popularizing the present invention in large scale. Meanwhile, it also solves the technical problem that in the existing bladder pressure monitoring devices, the bladder pressure detection unit is required to be frequently replaced to prevent the cross infection among patients.

Embodiment Two

Figure 2A:
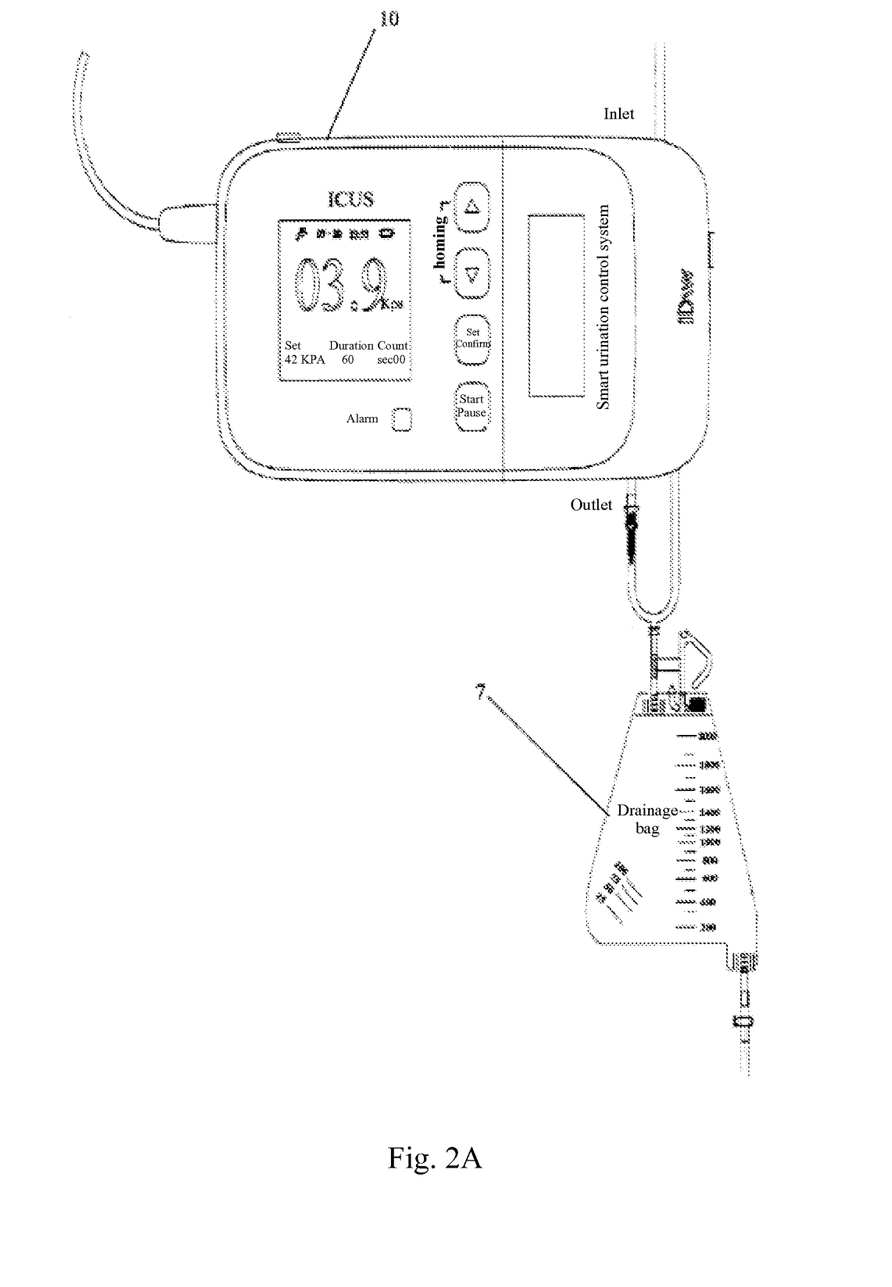
FIG. 2A is a structure diagram of a bladder and abdominal pressure monitoring system in the second embodiment of the present invention.
Figure 2B:
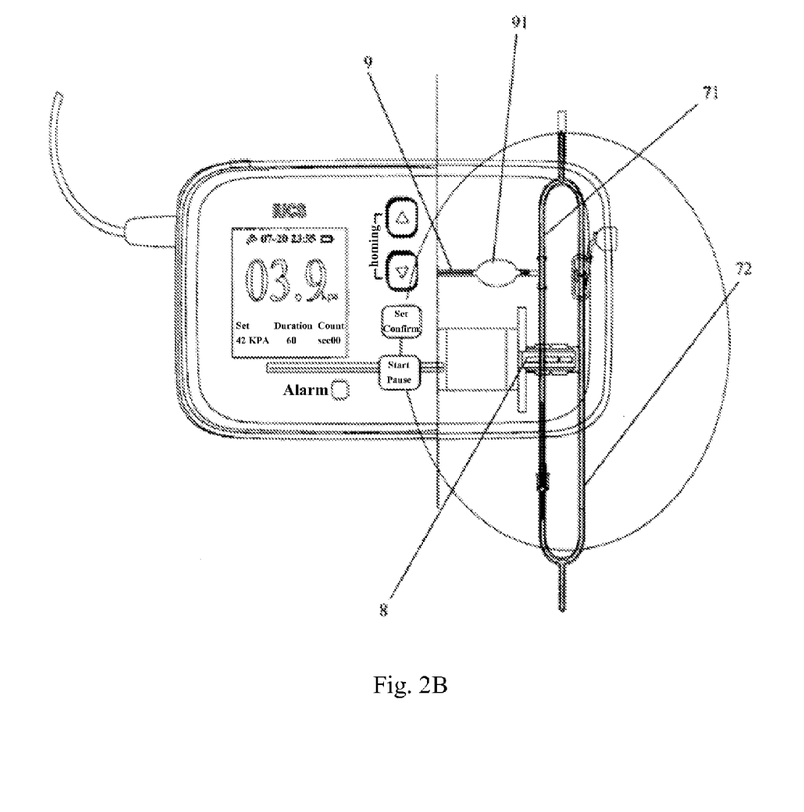
FIG. 2B is a structure diagram of FIG. 2A without partial housing.
Figure 2C:
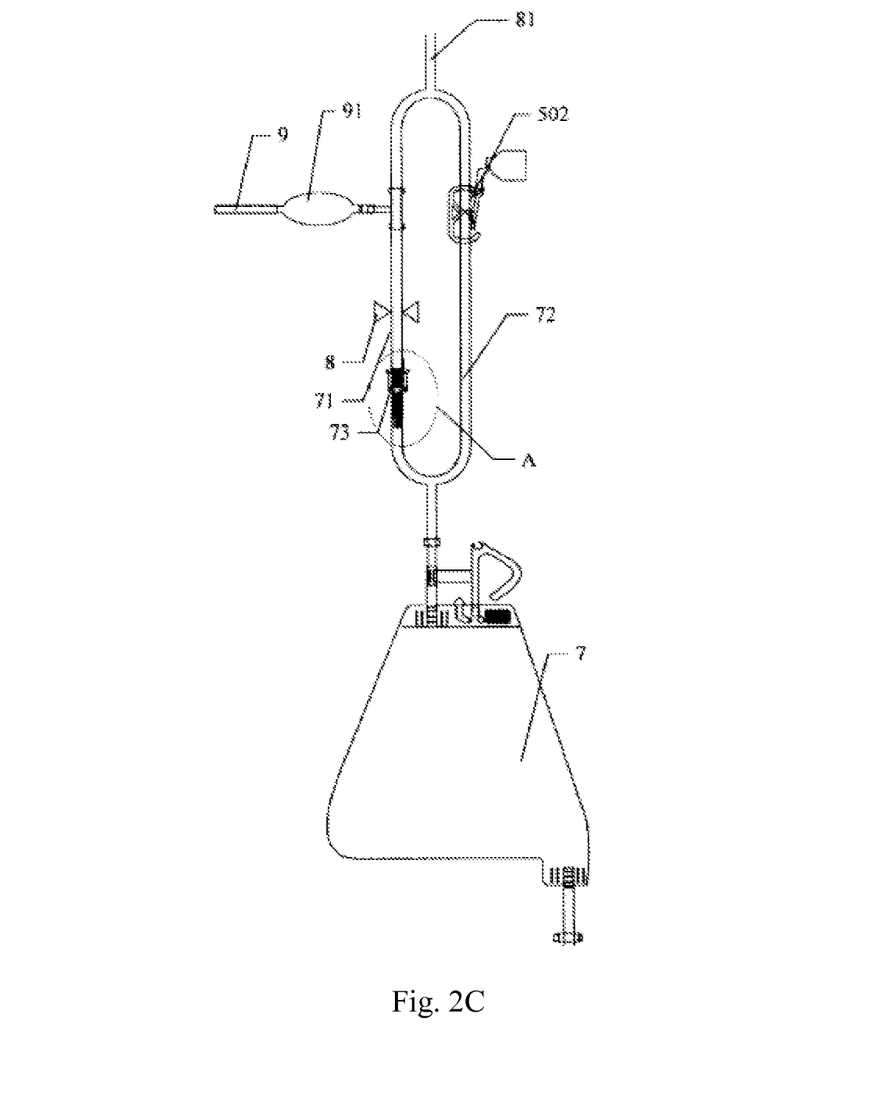
FIG. 2C is a partial structure diagram of the urination device in FIG. 2A.
Figure 2D:
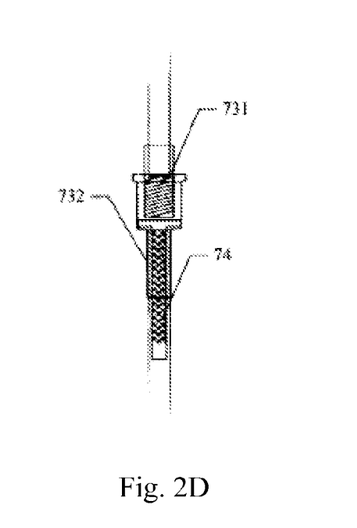
FIG. 2D is an enlarged figure of A in FIG. 2C.

FIG. 2A is a structure diagram of a bladder and abdominal pressure monitoring system in the second embodiment of the present invention; FIG. 2B is a structure diagram of FIG. 2A without partial housing; FIG. 2C is a structure diagram of partial urination device in FIG. 2A; FIG. 2D is an enlarged diagram of A in FIG. 2C. This embodiment provides a bladder and abdominal pressure monitoring system, comprising a bladder pressure detection unit, a central processing unit and a display unit as stated in the first embodiment. What is different from the first embodiment is that, the urination device in this embodiment adopts a two-channel drainage tube structure. As shown in FIGS. 2A, 2B, 2C and 2D, the bladder and abdominal pressure monitoring system provided in this embodiment comprises a housing 10, and a catheterization device, the bladder pressure detection unit 1, the central processing unit 2 and the display unit 3 (as shown in FIG. 1) which are integrated in the housing 10. The urination device comprises the drainage bag 7 and the drainage tube 10, wherein the drainage tube 10 comprises a main tube 81 and a first branch pipe 71 and a second branch pipe 72 connected between the bottom end of the main tube 81 and the drainage bag 7, and the main tube 81 is communicated with the drainage bag 7 via the first branch pipe 71 and the second branch pipe 72; the first solenoid valve 8 is mounted on the first branch pipe 71 and the thicker end of the capillary tube 9 is connected with the first branch pipe 71, and the second branch pipe 72 is provided with a second manually control valve 502.

In this embodiment, during normal operation of this system, the second manually control valve 502 on the second branch pipe 72 can be switched off, urination can be carried out by adopting the first branch pipe 71 and the first solenoid valve 8 thereon in coordination with the bladder pressure detection unit 1, the central processing unit 3 and the display unit 3 when the bladder pressure is equal to or higher than the preset pressure and the bladder pressure is valid. In case of emergency, for example, when an element fails during monitoring, the second manually control valve 502 can be switched on for emergent urination to prevent urine regurgitation in the bladder under high pressure, so as to further enhance the safety of the urination device and the bladder and abdominal pressure monitoring system.

Further, the first branch pipe 71 may be composed of a first drainage section and a second drainage section which are integrated into a whole via a connection plug 73, wherein the second drainage section is communicated with the drainage bag 7, and the first solenoid valve 8 and the capillary tube 9 are respectively arranged on the first drainage section. The connection plug 73 may comprise a top connector 731 fixed integratedly with the bottom of the first drainage section, and a bottom connector 732 fixed integratedly with the top of the second drainage section. The top connector 731 and the bottom connector 732 may be fixed together by screw joint. For example, the top connector 731 and the bottom connector 732 may be cylindrical, wherein the outside surface of the former and the inside surface of the latter are provided with threads respectively, so that the top connector 731 is in screw connection with the bottom connector 732, so as to achieve good tight connection.

Also, the connection plug 73 is configured in such a way that the top connector 731 and the bottom connector 732 may be dismantled by screwing them in opposite directions, i.e. the first branch pipe 71 is disconnected at the top connector 731 and then normal saline may be filled into the first drainage section of the first branch pipe 71 at the top connector 731; meanwhile, the capillary tube 9 communicated with the first branch pipe 71 passes transfers the urine pressure to the bladder pressure detection unit 1, thus the bladder pressured may be monitored in real-time during filling normal saline to the bladder, and the linear relationship between the bladder volume and the urine pressure may can be obtained to provide individual-based treatment of different patients.

Further, a filter may be installed in the bottom connector 732 for filtering the solid particles in the urine. The filter 74 may be a filter screen bag with an opening on its top, which may be fixed with the bottom connector 732 and makes the opening of the filter screen bag arranged towards the top connector 731 to ensure the solid particles in the urine to be retained in the filter screen bag when the urine flows through the connection plug 73 via the first drainage section. The bladder and abdominal pressure monitoring system in this embodiment is suitable for ICU monitoring for patients who have undergone laser bladder calculus crushing operation, and can conveniently collect the crushed calculus in the urine excreted from patients.

In this embodiment, a buffer gas bag 91 is arranged on the capillary tube 9 and close to the joint part of the capillary tube 9 and the drainage tube 10. Specifically, the buffer gas bag 91 may by round and internally provided with an accommodation cavity. The buffer gas bag 91 and the capillary tube 9 can form an integrated or a detachable structure, the accommodation cavity in the buffer gas bag 91 is communicated with the capillary tube 9. The capillary tube 9 and the buffer gas bag 91 may be filled with pressure transmission medium such as air or silicone oil. When the gas within the urinary catheter 2 (as shown in FIG. 1) causes the ambient pressure to increase due to thermal expansion or vibration, or the gas within the capillary tube 9 is compressed due to the increase of the urine pressure, the gas within the buffer gas bag 91 may timely enter the capillary tube 9 as supplementary. Therefore, the urine in the urinary catheter may be prevented from being sucked into the capillary tube 9 and then effectively prevent from flowing back to the pressure sensor to cause malfunction of the pressure sensor, so as to ensure accuracy of the bladder pressure detected by the pressure sensor, prevent urine contamination of the pressure sensor, and avoid cross infection due to reuse of the pressure sensor.

Embodiment Three

Figure 3:
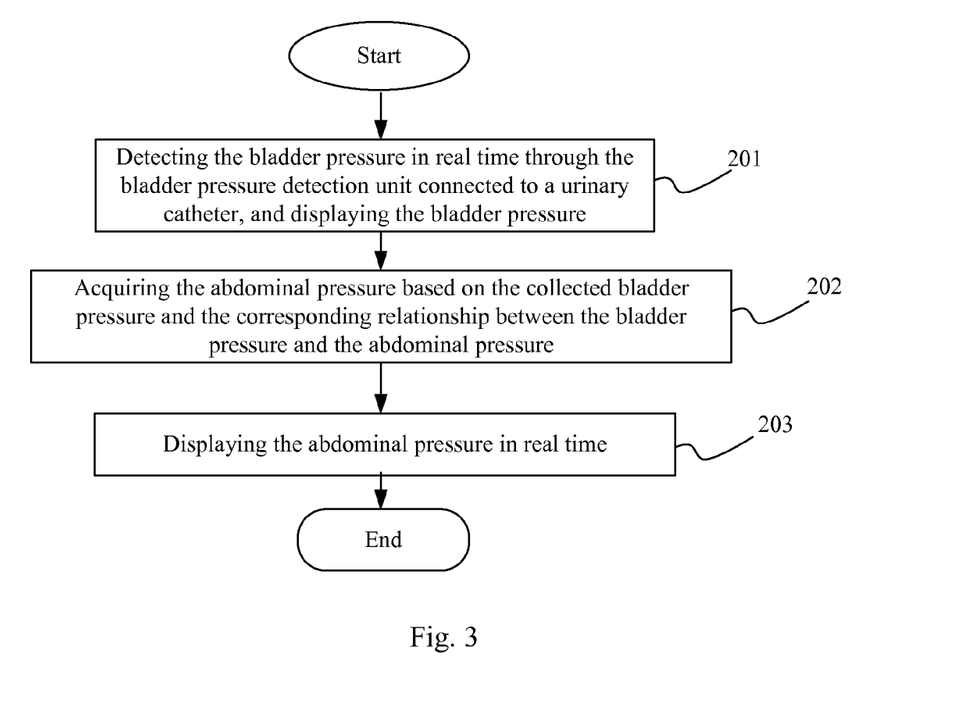
FIG. 3. is a flow diagram of the a bladder and abdominal pressure monitoring method in the third embodiment of the present invention.

FIG. 3 is a flow diagram of the bladder and abdominal pressure monitoring method in the third embodiment of the present invention.

As shown in FIG. 3, the bladder and abdominal pressure monitoring method provided in the second embodiment is achieved by the bladder and abdominal pressure monitoring system provided in the first embodiment, comprising the following steps:

Step 201, detecting the bladder pressure in real time by the bladder pressure detection unit communicated with the urinary catheter, and displaying the bladder pressure, wherein the bladder pressure detection unit is preferably a low-pressure sensor;

Step 202, based on the collected bladder pressure, obtaining the abdominal pressure according to the corresponding relationship between the bladder pressure and the abdominal pressure;

Step 203, displaying the abdominal pressure in real time.

In some embodiments, in steps 201 and 203, the bladder pressure and the abdominal pressure may be displayed via the display unit and the display unit is preferably an OLED display screen.

The bladder and abdominal pressure monitoring method provided in this embodiment may be used to detect the bladder pressure in real time and obtain the abdominal pressure according to the corresponding relationship between the bladder pressure and the abdominal pressure. Thus the method may be used to simultaneously monitor the abdominal pressure and the bladder pressure in real time. Therefore, it solves the technical problem that the existing technology cannot timely and safely know the change of abdominal pressure.

Figure 5:
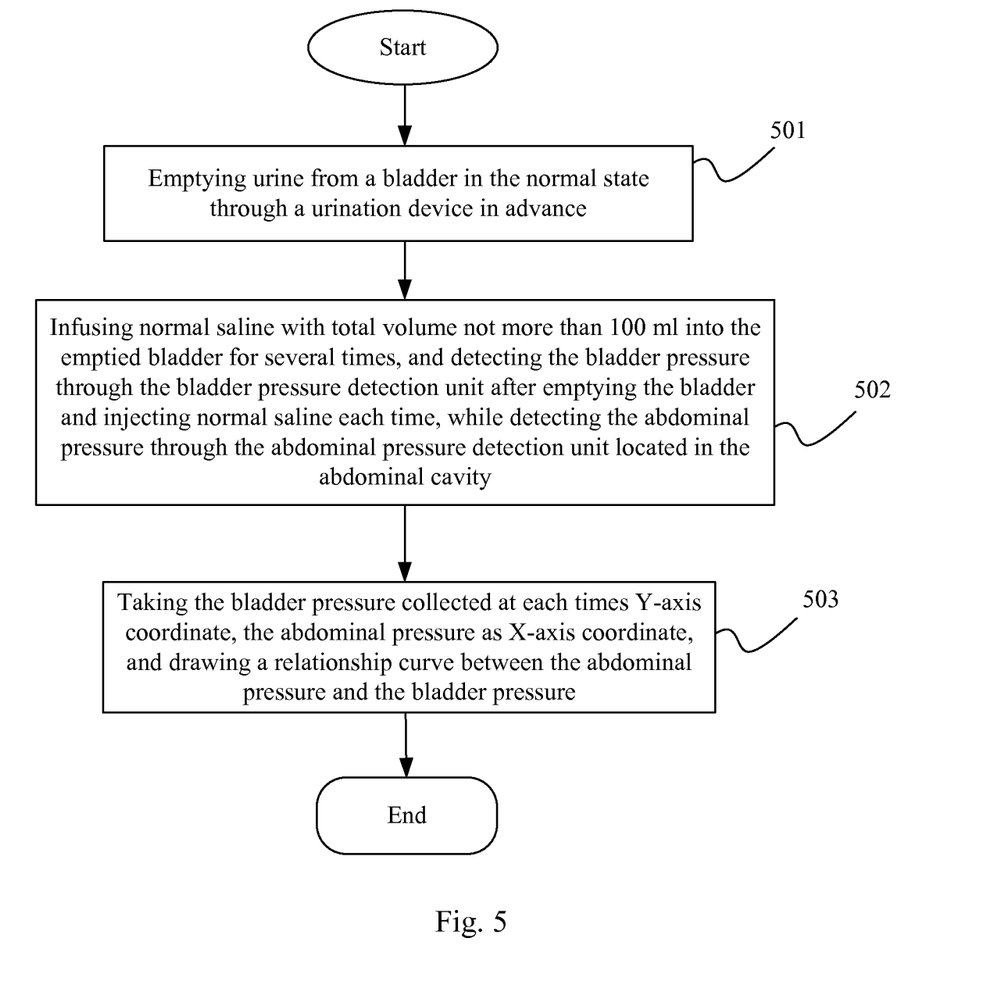
FIG. 5 is a flow diagram of the decomposing steps of the function of the corresponding relationship between the bladder pressure and the abdominal pressure obtained in the embodiments of the present invention.

As shown in FIG. 5, based on the previously mentioned technical solution, this embodiment further comprises obtaining the function of the corresponding relationship between the bladder pressure and the abdominal pressure, specifically comprising the following steps:

Step 501, emptying urine in the bladder under normal condition with the urination device in advance;

Step 502, filling normal saline with total volume not more than 100 ml into the emptied bladder for several times, for example, preferably filling normal saline with total volume of 100 ml into the emptied bladder for 10 times, 10 ml each time, and after emptying the bladder and filling normal saline each time, and simultaneously detecting the bladder pressure via a bladder pressure detection unit and the abdominal pressure via an abdominal pressure detection unit in the abdominal cavity.

Step 503, taking the bladder pressure collected each time as Y-axis coordinate and the abdominal pressure as X-axis coordinate, drawing a relationship curve between the bladder pressure and the abdominal pressure, thereby obtaining the function of the corresponding relationship between the bladder pressure and the abdominal pressure.

In order to guarantee the above function can accurately reflect the linear relation between the bladder pressure and the abdominal pressure, the above test may be conducted on many normal subjects (e.g. 100 subjects) with different ages and sexes, and precise function of the corresponding relationship between the bladder pressure and the abdominal pressure is obtained based on the average values of the collected bladder pressure and the abdominal pressure. For example, through detection and calculation, the obtained function of the corresponding relationship between the bladder pressure and the abdominal pressure can be the linear function satisfying the following expression:

Y=0.939X+1.482, wherein X represents the abdominal pressure, Y represents the bladder pressure, 0.939 is correlation coefficient (i.e. slope), and the pressure unit is millimeter of mercury (mmHg).

Thus, as long as the bladder pressure Y collected by the bladder pressure detection unit is substituted into the above expression, the abdominal pressure X may be obtained accordingly.

It should be also noted that, the bladder volume in a certain range (the filling volume is less than 100 ml) is deemed as a passive storage tank with high compliance, like a passive diaphragm, it may transfer the intra-abdominal pressure other than addition of any pressure from its own detrusor muscle. Meanwhile, the studies on the corresponding relationship between the abdominal pressure and the bladder pressure has been found in some literatures, but it is so far only limited to linear relation of both in a single fixed volume and has narrow application scope. However, the linear function obtained in the present invention can monitor the abdominal pressure by virtue of the change in bladder pressure within a certain volume range in a dynamic and real-time manner.

Embodiment Four

Figure 4:
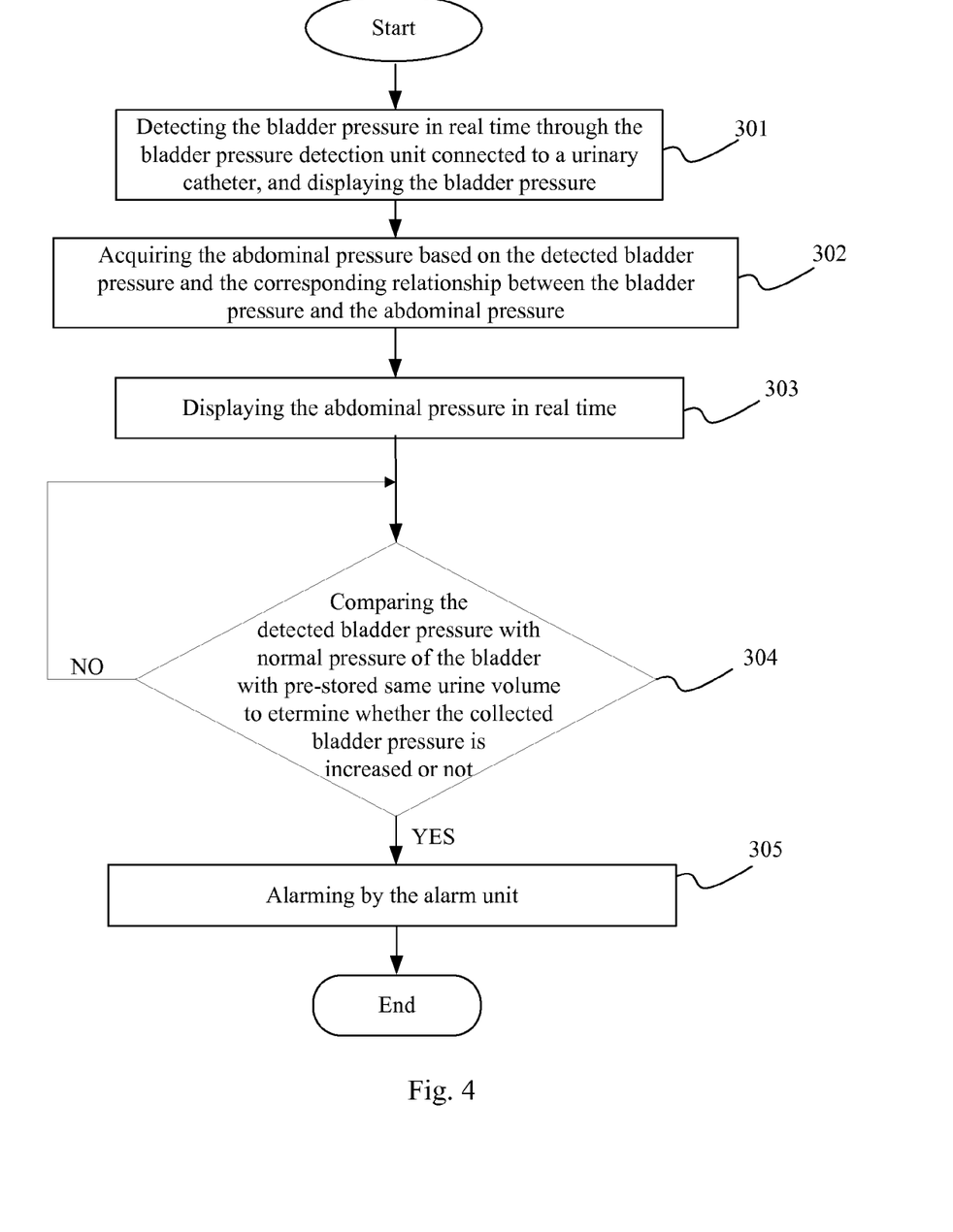
FIG. 4. is a flow diagram of a bladder and abdominal pressure monitoring method of in the fourth Embodiment of the present invention.

FIG. 4 shows a flow diagram of the bladder and abdominal pressure monitoring method provided by the fourth embodiment of the present invention. As shown in FIG. 4, the bladder and abdominal pressure monitoring method provided by the fourth embodiment of the present invention may be realized using the bladder and abdominal pressure monitoring system provided by the first embodiment of the present invention. The bladder and abdominal pressure monitoring method comprises the steps of:

Step 301, detecting the bladder pressure in real time through the bladder pressure detection unit connected to a urinary catheter, and displaying the bladder pressure, wherein the bladder pressure detection unit is preferably a low-pressure sensor;

Step 302, acquiring the abdominal pressure based on the detected bladder pressure and the corresponding relationship between the bladder pressure and the abdominal pressure;

Step 303, displaying the abdominal pressure in real time;

Step 304, comparing the collected bladder pressure with the normal pressure of the bladder with pre-stored same urine volume to determine whether the detected bladder pressure is increased or decreased: if pressure is increased, performing step 305 is performed; Otherwise step 304 is performed. The increase or decrease of the abdominal pressure can be indirectly determined based on the increase or decrease of the bladder pressure, so as to perform the subsequent corresponding alarming operation. The normal bladder pressure can be detected from patients when bladder is in normal state before operation;

Step 305, alarming by the alarm unit, wherein the alarm unit may include a buzzer and/or warning lights, which can send out different sounds and/or alerts based on the increase or decrease of the bladder pressure to prompt the patient or medical staff.

In the step 301 and step 303, the bladder pressure and the abdominal pressure can be displayed by the display unit which is preferably an OLED display screen.

The bladder and abdominal pressure monitoring method provided by the embodiment is capable of acquiring the abdominal pressure based on the determined bladder pressure and the corresponding relationship between the bladder pressure and the abdominal pressure, thus achieving real-time monitoring of the bladder pressure and the abdominal pressure simultaneously; and determining whether the patient's bladder pressure is increased or decreased in comparison with normal values, thereby indirectly determining whether the patient's abdominal pressure is increased or decreased, at the same time, giving alarms when the bladder pressure is abnormal. Thus the method can be used to solve the technical problem in the prior art that the change of intra-abdominal pressure cannot be timely and securely obtained.

As shown in FIG. 5, based on the technical solution previously mentioned, the present embodiment may also include a step of obtaining a function of the corresponding relationship between the bladder pressure and the abdominal pressure. In some embodiments, the step of obtaining a function of the corresponding relationship between the bladder pressure and the abdominal pressure includes the following steps:

Step 501, emptying urine from a bladder in the normal state through a urination device in advance;

Step 502, infusing normal saline with total volume not more than 100 ml into the emptied bladder for several times, for example, preferably: infusing normal saline with total volume of 100 ml into the emptied bladder for 10 times, 10 ml each time, and detecting the bladder pressure through the bladder pressure detection unit after emptying the bladder and infusing normal saline each time, meanwhile, detecting the abdominal pressure through the abdominal pressure detection unit located in the abdominal cavity;

Step 503, taking the bladder pressure detected each time as Y-axis coordinate, the abdominal pressure as X-axis coordinate, drawing the relationship curve between the abdominal pressure and bladder pressure, thereby obtaining the function of the corresponding relationship between the bladder pressure and the abdominal pressure.

In order to ensure that the above function can accurately reflect the linear relationship between the abdominal pressure and the bladder pressure, pressure detection test can be conducted in many normal subjects (e.g. 100 subjects) with different ages and sexes. Accurate function of the corresponding relationship between the bladder pressure and the abdominal pressure is obtained by use of the average values of the detected bladder pressure and the abdominal pressure. For example, after detection and calculation, the function of the corresponding relationship between the bladder pressure and the abdominal pressure can be a linear function satisfying the following expression:

Y=0.939X+1.482, wherein, X represents the abdominal pressure, Y represents the bladder pressure, 0.939 is the correlation coefficient (i.e. slope), and the pressure unit is millimeters of mercury (mmHg).

Thus, as long as the bladder pressure Y detected by the bladder pressure detection unit 1 is substituted into the above expression, the value of the abdominal pressure X may be obtained accordingly.

It should be also noted that, the bladder volume in a certain range (the filling volume is less than 100 ml) is deemed as a passive storage tank with high compliance, like a passive diaphragm, it may transfer the pressure in the abdominal cavity other than addition of any pressure of its own detrusor muscle. Meanwhile, the studies on correlation between the abdominal pressure and the bladder pressure has been found in some literatures, but it is so far only limited to linear relation of both in a single fixed volume and has narrow application scope. However, the linear function obtained in the present invention can monitor the abdominal pressure by virtue of the change in bladder pressure within a certain volume range in a dynamic and real-time manner.

Based on the previously mentioned technical solution, the bladder and abdominal pressure monitoring method of the embodiment further comprises communicating the bladder pressure detection unit and the urinary catheter using U-shaped capillary tubes with two ends with different thicknesses, including:

filling pressure transmission medium into the capillary tubes, such as air or silicone oil, for preventing the bladder pressure detection unit from directly contacting with the urine in the urinary catheter when detecting the bladder pressure; communicating the thicker end of the capillary tube with the urinary catheter; connecting the other end of the capillary tube to the bladder pressure detection unit. Therefore, for different patients, it is not necessary to change the bladder pressure detection unit, greatly reducing the cost for promoting the large-scale use of the present invention, while also overcoming the technical problem in the existing bladder pressure monitoring method that the bladder pressure detection unit needs to be frequently replaced in order to prevent the cross-infection among patients.

Embodiment Five

Figure 6:
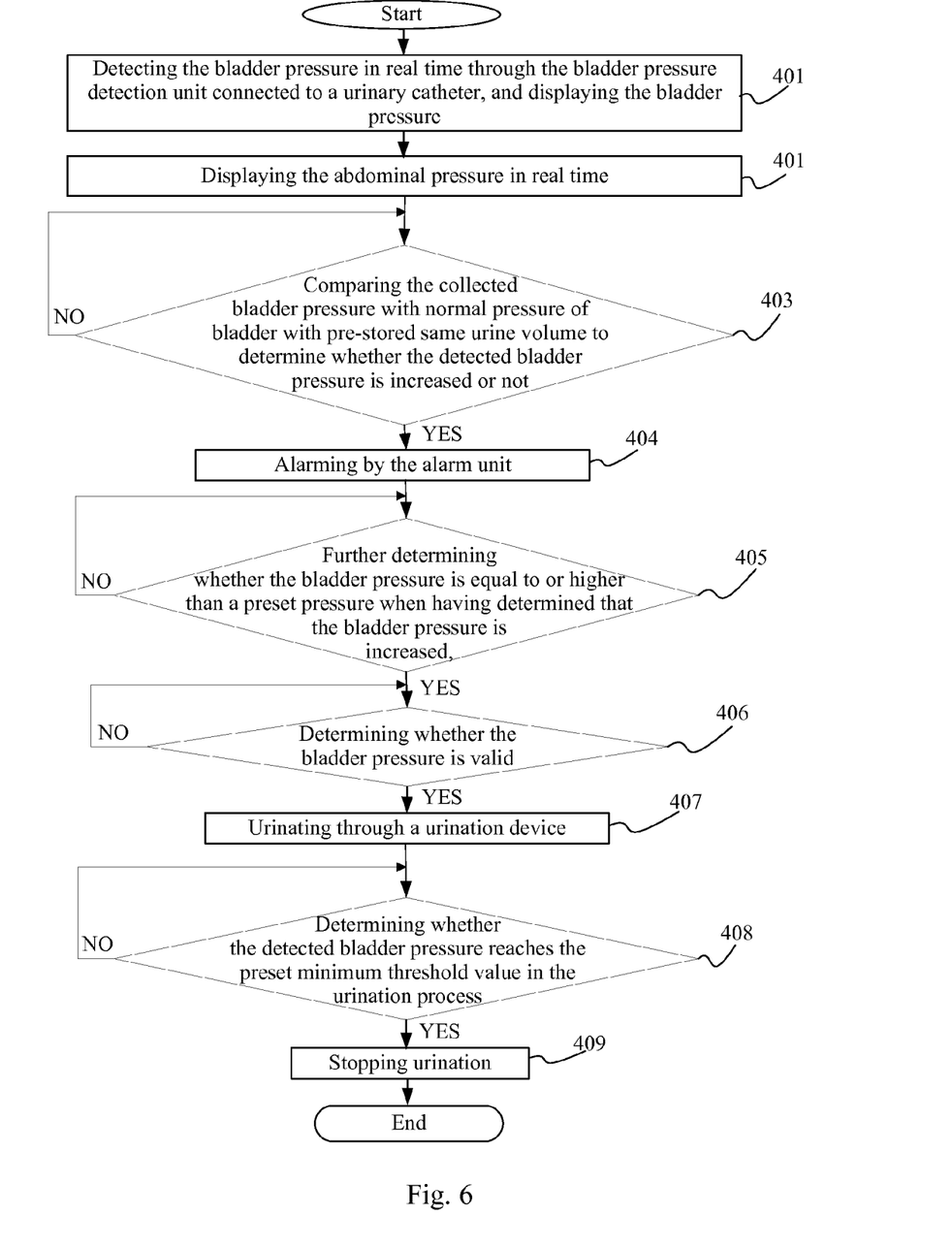
FIG. 6 is a flow diagram of a bladder and abdominal pressure monitoring method in the fifth embodiment of the present invention.

FIG. 6 shows a flow diagram of the bladder and abdominal pressure monitoring method provided by the fifth embodiment of the present invention. As shown in FIG. 6, the bladder and abdominal pressure monitoring method provided by the fifth embodiment of the present invention may be realized using the bladder and abdominal pressure monitoring system provided by the first embodiment of the present invention. The bladder and abdominal pressure monitoring method comprises the steps of:

Step 401, detecting bladder pressure in real time through the bladder pressure detection unit connected to a urinary catheter, and displaying the bladder pressure, wherein the bladder pressure detection unit is preferably a low-pressure sensor;

Step 402, displaying the abdominal pressure in real time;

Step 403, comparing the detected bladder pressure with normal pressure of bladder with pre-stored same urine volume to determine whether the detected bladder pressure is increased or decreased: if the adjustment result is yes, performing the step 404; if no, proceeding with the step 403, so that the increase or decrease of the abdominal pressure can be indirectly determined based on the increase or decrease of the bladder pressure, so as to perform the subsequent corresponding alarming operation, wherein the normal bladder pressure can be detected from patients with bladder in a normal state before operation;

Step 404, alarming by the alarm unit, wherein the alarm unit may include a buzzer and/or warning lights, which can send out different sounds and/or alerts based on the increase or decrease of the bladder pressure to prompt the patient or medical staff;

Step 405, when having determined that the bladder pressure is increased, further judging whether the bladder pressure is equal to or higher than a preset pressure, if the result shows that the bladder pressure is equal to or higher than the preset pressure, then performing step 406, otherwise, proceeding to step 405, wherein the preset pressure may be preferably 20 cm water column (cmH$_2$O), which is relatively safe pressure of the bladder;

Step 406, judging whether the bladder pressure is valid, if the result shows that the bladder pressure is valid, performing step 407, otherwise proceeding to step 406;

Step 407, urinating through a urination device, wherein the urination device comprises a drainage bag and a first solenoid valve; the drainage bag is used for collecting urine drained from the bladder, the input end of the first solenoid valve is communicated with the urinary catheter, the output end of the first solenoid valve is communicated with the drainage tube of the drainage bag; the first solenoid valve is started to urinate when having judged that the bladder pressure is valid, thereby lowering the bladder pressure while helping to reduce the abdominal pressure. The first solenoid valve is preferably a hose extrusion-type solenoid valve;

Step 408, in the urination process, determining whether the acquired bladder pressure reaches a preset minimum threshold value, if the result is yes, then performing step 410, otherwise proceeding to step 409, wherein the preset minimum threshold value is preferably the minimum pressure threshold of the monitored abdominal pressure;

Step 409, stopping urination, so that the pressure within the bladder can be always kept not only within a relatively safe pressure range, but also equal to or higher than the minimum pressure threshold of the monitored abdominal pressure, thereby simultaneously achieving the high safety low-pressure urine storage and urination and the real-time monitoring of the abdominal pressure.

Wherein, in step 401, the bladder pressure and the abdominal pressure can be displayed by the display unit which is preferably an OLED display screen.

The bladder and abdominal pressure monitoring method provided by the embodiment is capable of acquiring bladder pressure in real time, and obtaining abdominal pressure based on the corresponding relationship between the bladder pressure and the abdominal pressure, thus achieving real-time monitoring of the bladder pressure and the abdominal pressure simultaneously; and determining whether the patient's bladder pressure is increased or decreased in comparison with a normal value, thereby indirectly determining whether the patient's abdominal pressure is increased or decreased, at the same time, giving alarms when the bladder pressure is abnormal, thus solving the technical problem in the prior art that the abdominal pressure change cannot be timely and securely obtained. Moreover, for the stable ICU (Intensive Care Unit) patients, the pressure change inside the bladder can be used to start or close the urination device in time. The working theory exactly simulates the urine storage and urination process of human beings, which can help patients retain original bladder functions, prevent or delay repeated infections of the urinary system, bladder spasms, structural and functional changes of urinary tracts, avoid disuse of bladder function and threat to kidneys caused by previously mentioned situations, thereby improving the patient's quality of life and extending survival time.

Embodiment Six

Figure 7:
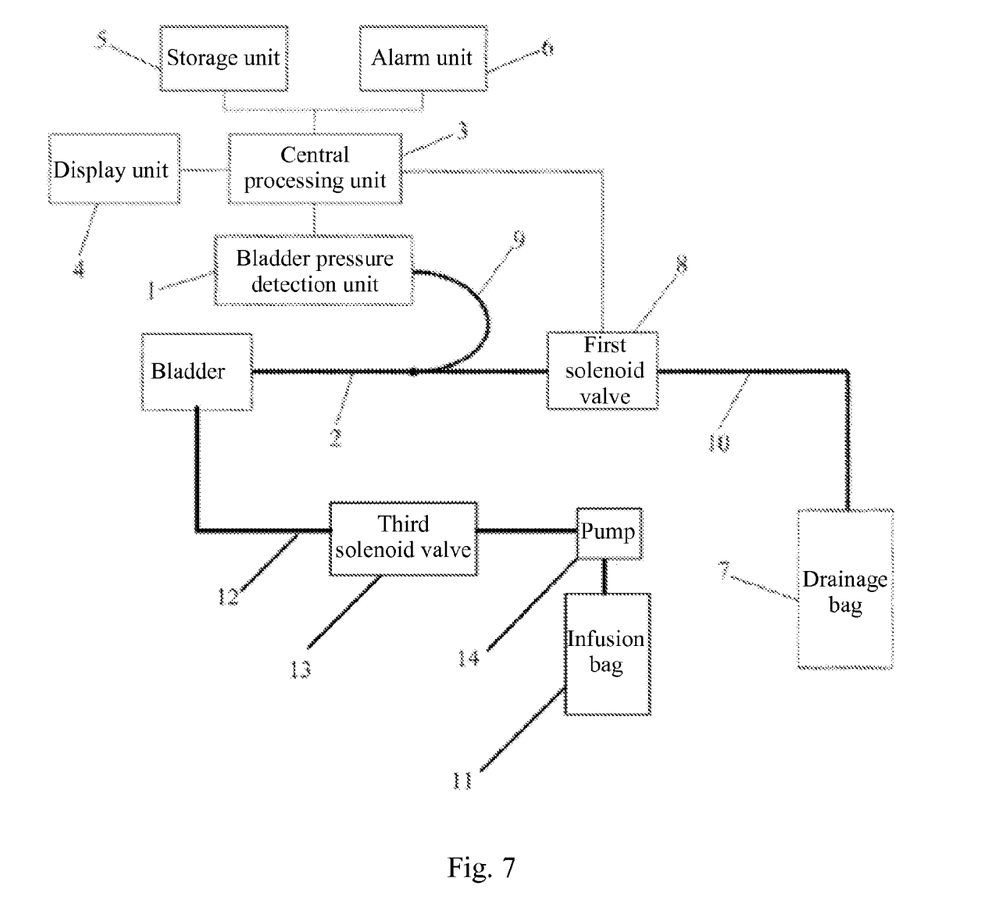
FIG. 7 is a structure diagram of a bladder function recovery system in the sixth embodiment of the present invention.

FIG. 7 is a structure diagram of the bladder function recovery system provided by the sixth embodiment of the present invention; the present embodiment provides a bladder function recovery system, comprising:

a bladder pressure detection unit 1 for communicating with the urinary catheter 2 and detecting the bladder pressure in real-time;

a central processing unit 3, connected to the bladder pressure detection unit 1, and used for acquiring abdominal pressure based on the detected bladder pressure and the corresponding relationship between the bladder pressure and the abdominal pressure;

a display unit 4, connected with the central processing unit 3, and used for displaying the bladder pressure and the abdominal pressure in real time;

a urination device, comprising: a drainage bag 7 for collecting the urine drained from the bladder, a drainage tube 10 communicated with the drainage bag 7 and a first solenoid valve 8 located on the drainage tube 10, wherein the input end of the first solenoid valve is communicated with urinary catheter 2, and the output end of the first solenoid valve 8 is communicated with the drainage tube 10;

an infusion device, used for infusing perfusate into the bladder, comprising an infusion bag 11 filled with the perfusate, an infusion tube 12 for infusing the perfusate into the bladder, and a third control component (not shown in drawing) located on the infusion tube 12;

The central processing unit 3 is further used to compare the bladder pressure detected by the bladder pressure detection unit 1 with the preset first bladder pressure threshold and the second bladder pressure threshold; if the comparison result is that the bladder pressure is equal to or higher than the first bladder pressure threshold, switch on the first solenoid valve 8 and close the third control component, that is, executing the urination process through the urination device; if the comparison result is that the bladder pressure is less than or equal to the second bladder pressure threshold, then close the first solenoid valve 8 and switch on the third control component, namely stop urination and start the infusion process.

The perfusate may be normal saline; the first bladder pressure threshold is higher than the second bladder pressure threshold. For example, the first bladder pressure threshold can be the safe bladder pressure specified in the urodynamics, and the second bladder pressure threshold can be determined by the pressure value of emptied bladder according to the urodynamics.

Clinically, the bladder function recovery device of the embodiment can be used for recovery training of the bladder functions for neurogenic patients, in particular, the recovery training is performed in two stages:

In the first stage, perform intervention volume sensing training; firstly, drain urine from the bladder, then inject normal saline into the bladder at a constant rate through the infusion device until the bladder pressure reaches the first bladder pressure threshold, making the bladder generate the urination sense, thereby achieving the purpose of urination reflex training. Artificially reasonable volume stimulation to the bladder, to some extent, strengthens and improves the synergy between the bladder detrusor and sphincter.

In the second stage, perform physiological volume sensing training; use personalized urination manner, that is, when the bladder of the patient is fully filled or the bladder pressure reaches the first bladder pressure threshold (which can be the specified safe bladder pressure medically), use the urination device to discharge the urine generated by the body and the infused normal saline from the bladder to gradually establish a urination mechanism in response to the bladder capacity. The cycle of these two processes can achieve the purpose of recovery training of the bladder functions of neurogenic patients.

The bladder function recovery system provided by the embodiment promotes the link between the low spinal cord central nervous systems and brains of patients through simulating human urine storage and urination process, making the bladder form a conditioned reflex in rhythmic filling and emptying, so as to prevent or delay patient repeated infections of urinary system, bladder spasms, structural and functional changes of urinary tracts, avoid disuse of bladder functions and threat to kidneys caused by previously mentioned situations, thereby improving the patient's quality of life and extending the survival time of patients.

Specifically, the third control component may comprise a third solenoid valve 13 located on the infusion tube 12 and an infusion pump 14 located on the joint part of the infusion tube 12 and the infusion bag 11, and used for pumping the perfusate into the infusion bag 11 to the bladder, wherein both the first solenoid valve 8 and the third solenoid valve 13 can be one-way solenoid valves, and on-off operation thereof can be controlled by the central processing unit 3 via electric signals. Further, the one-way solenoid valves can prevent backflow, thus protecting elements in the system from being contaminated, and improving operational reliability.

It should be noted that, the bladder function recovery system provided by this embodiment can realize the control of the process of urination and infusion by adding the infusion device in the embodiment and writing a control program in the central processing unit 3 based on the bladder and abdominal pressure monitoring system mentioned in the foregoing first and second embodiments, thereby easily performing the recovery training of the bladder functions. Here, similar to the previous embodiment, after detecting the bladder pressure, the bladder pressure detection unit 1 compares the bladder pressure with the preset first bladder pressure threshold and the second bladder pressure threshold; if the comparison result shows that the bladder pressure is equal to or higher than the first bladder pressure threshold, it can further judge whether the bladder pressure is valid, for example, it can judge whether the duration of the bladder pressure is more than or equal to a preset time; if the value is valid, implement the urination process through the urination device; if comparison result shows that the bladder pressure is less than or equal to the second bladder pressure threshold, also judge whether the bladder pressure is valid; if yes, immediately stop urination, and start the infusion process.

Finally, it should be noted that: the above embodiments are only used to illustrate the technical solutions of the present invention, not intended to limit the present invention; although reference to the embodiments, the present invention has been described in details, ordinary technicians in the art should understand: the technical solutions described in foregoing embodiments also can be modified, or partial technical features can be equivalently replaced; and these modifications or replacements do not make the essence of the corresponding technical solutions depart from the scope of technical solutions of various embodiments of the present invention.

The invention claimed is:

1. A bladder pressure monitoring system for monitoring bladder pressure in a subject, comprising:
   a bladder pressure detection unit;
   a capillary tube having a first and a second end openings with the first end opening of the capillary tube connected to the bladder pressure detection unit, wherein the capillary tube is filled with pressure transmission medium so that the bladder pressure detection unit does not directly contact with urine and the bladder pressure detection unit detects the bladder pressure in a continuous manner;
   a urinary drainage tube that is connected to the second end opening of the capillary tube, wherein the drainage tube has a first end opening, a second end opening and one middle opening, with the first end opening of the urinary drainage tube being connected to a urinary catheter, a second end opening of the urinary drainage tube connected to a drainage bag, and the middle opening of the urinary drainage tube connected to the second end opening of the capillary tube;

a first solenoid valve being placed inside the urinary drainage tube at a position between the middle opening and the second end opening of the urinary drainage tube, wherein the first solenoid valve can be switched on or off in controlling the urine flow in the urinary drainage tube; and a central processing unit that is connected to the bladder pressure detection unit, wherein the central processing unit determines whether the bladder pressure increases and switches on the first solenoid valve for urination when the central processing unit has determined that the bladder pressure increases.

2. The bladder pressure monitoring system according to claim 1, further comprising a display unit that is connected to the central processing unit, wherein the display unit displays the bladder pressure in real time.

3. The bladder pressure monitoring system according to claim 1, further comprising:
   a storage unit that is connected with the central processing unit, and stores preset bladder pressure values; and
   an alarm unit, that is connected to the central processing unit and sends alarms when the central processing unit has determined that the bladder pressure reaches preset bladder pressure values.

4. The bladder pressure monitoring system according to claim 1, wherein the central processing unit determines whether the bladder pressure is valid.

5. The bladder pressure monitoring system according to claim 1, further comprising a drainage bag for collecting urine.

6. The bladder pressure monitoring system according to claim 5, wherein the central processing unit determines whether the detected bladder pressure reaches a preset minimum threshold value; and if the detected bladder pressure reaches the preset minimum threshold value, the central processing unit switches off the first solenoid valve to stop urination.

7. The bladder pressure monitoring system according to claim 6, wherein the drainage tube is connected to the bladder pressure detection unit through a U-shaped capillary tube having two ends, with one end thicken than the other end, and the thicker end of the capillary tube being connected to the drainage tube, and the thinner end of the capillary tube being connected to the bladder pressure detection unit.

8. The bladder pressure monitoring system according to claim 1, wherein the drainage tube comprises a main tube having a top opening and a bottom opening with the top opening connected to the urinary catheter, a first branch tube, and a second branch tube;
   wherein the first and second branch tubes joins on two ends with a first end being fluidly connected to the bottom opening of the main tube, and a second end being fluidly connected to the drainage bag so that the main tube may fluidly communicate with the drainage bag through the first and second branch tubes, respectively;
   wherein the first solenoid valve is in the first branch tube and the capillary tube is connected to the first branch tube; and
   wherein a second manually controlled valve is placed in the second branch tube.

9. The bladder pressure monitoring system according to claim 8, wherein the first branch tube is composed of a first drainage section and a second drainage section;
   wherein a connector connects the first drainage section and the second drainage section;
   wherein the second drainage section is communicated with the drainage bag; and
   wherein the first solenoid valve is located on the first drainage section and the capillary tube is connected to the first drainage section.

10. The bladder pressure monitoring system according to claim 9, wherein the connector that connects the first drainage section and the second drainage section has a top opening and a bottom opening, wherein the top opening is integrated with the first drainage section in a fixed manner and the bottom opening is integrated with the second drainage section in a fixed manner; and the top opening and the bottom opening are fixed in a threaded manner.

11. The bladder pressure monitoring system according to claim 10, wherein the bottom opening of the connector contains a filter for filtering solid particles in the urine.

12. The bladder pressure monitoring system according to claim 1, wherein a buffer gas bag is provided on the capillary tube.

13. The bladder pressure monitoring system according to claim 1, being adapted to help bladder function recovery in a subject, further comprising:
   an urination device, comprising: a drainage bag for collecting urine from a bladder of the subject, a drainage tube communicated with the drainage bag and a first solenoid valve located on the drainage tube, wherein the first solenoid valve having an input end and an output end, and wherein the input end of the first solenoid valve is used for communicating with the urinary catheter, and the output end is communicated with the drainage tube;
   an infusion device, used for filling perfusate into the bladder, and comprising an infusion bag with the perfusate, an infusion tube for infusing the perfusate into the bladder, and a third control component located on the infusion tube; and
   wherein the central processing unit compares the bladder pressure collected by the bladder pressure detection unit with a preset first bladder pressure threshold and a second bladder pressure threshold; if the bladder pressure is equal to or higher than the first bladder pressure threshold, the first solenoid valve is switched on and the third control component is switched off; and if the bladder pressure is less than or equal to the second bladder pressure threshold, then the first solenoid valve is switched off and the third control component is switched on.

14. The bladder pressure monitoring system according to claim 13, wherein the third control component comprises a third solenoid valve located on the infusion tube, and an infusion pump located between the infusion tube and the infusion bag, and wherein the infusion pump pumps the perfusate in the infusion bag to the bladder.

15. The bladder pressure monitoring system according to claim 14, wherein both the first solenoid valve and the third solenoid valve are one-way solenoid valves.

\* \* \* \* \*